United States Patent
Lemchen

[19]

[11] Patent Number: 6,056,545
[45] Date of Patent: May 2, 2000

[54] MESOPOROUS METAL FOR ORTHODONTIC APPLIANCES

[76] Inventor: Marc. S. Lemchen, 553 Park Ave., New York, N.Y. 10021

[21] Appl. No.: 09/295,270

[22] Filed: Apr. 20, 1999

[51] Int. Cl.[7] ........................................ A61C 3/00
[52] U.S. Cl. .................................. 433/20; 433/8
[58] Field of Search .................... 433/2, 8, 18, 20

[56] References Cited

U.S. PATENT DOCUMENTS

| | | |
|---|---|---|
| 5,018,969 | 5/1991 | Andreiko et al. . |
| 5,131,843 | 7/1992 | Hilgers et al. . |
| 5,166,380 | 11/1992 | Alberti et al. . |
| 5,295,823 | 3/1994 | Farzin-Nia ................................... 433/9 |
| 5,829,972 | 11/1998 | Farzin-Nia . |

OTHER PUBLICATIONS

The Exonomist, Mar., 1999, Science and Technology, "Through a Metal, Darkly" pp. 95–97.

*Primary Examiner*—Ralph A. Lewis
*Attorney, Agent, or Firm*—Daniel L. Dawes

[57] ABSTRACT

Orthodontic appliance is made from mesoporous metals are substantially transparent or at least translucent so that they present a cosmetic appearance having a color the same as or similar to the natural dental services to which the appliance is applied. The archwires and brackets of the orthodontic appliance are fabricated from mesoporous metal and metal alloys, which have defined therein pores the diameter less than the shortest wavelength of visible light incident on the appliance and with a density of pores such that the average index of a fraction of the mesoporous metal is closer to that of air than to the solid metal from which the dental appliance is fabricated. The small size of the pores means that the dental appliance is a poor scatterer of light while the high density of pores means that the optical properties of the mesoporous metal on the average tend to match those of air as opposed to the solid metal, thus making the mesoporous metal transparent or at the very least translucent. Nevertheless, the mesoporous metal in the form of brackets and archwire is still able to carry high tensile loads as may be required to apply corrective forces to maloccluded teeth within an orthodontic appliance.

20 Claims, 1 Drawing Sheet

MESOPOROUS METAL FOR ORTHODONTIC APPLIANCES

BACKGROUND OF INVENTION

1. Field of Invention

The present invention relates generally to orthodontic devices and more particularly to the selection of materials used in orthodontic archwires, brackets and other appliances used to apply corrected forces to maloccluded teeth.

2. Description of Prior Art

The practice of orthodonture is the use of various appliances to correct the malocclusion of teeth. During this corrective procedure it is often necessary to impart a variety of forces to the teeth to move the teeth to their final desired positions. Typically this is achieved through a use of variety of different appliances either simultaneous or consecutively. One of the most common appliances used in orthodontics is an orthodontic archwire which is secured to orthodontic brackets, which in turn are attached to the teeth of the patient. Although attempts have been made to make archwires, brackets and other device portions of plastic, resins, ceramic and glass fibers, these attempts have been generally unsuccessful, because plastic, resins, ceramic and glass fibers are unable to carry the high tensile loads over the periods of time required in orthodontic devices. Thus, in general archwires and brackets must be made from high tensile strength metal in order to carry the loads and forces. However, metal braces are regarded by many as cosmetically unattractive and in some cases is the primary reason why patients may be reluctant to subject themselves to orthodonture.

What is needed is a material which may be used for orthodontic appliances such as archwire and brackets which is capable of carrying the tensile loads of metal, is not subject to the material limitations of plastics, resins, ceramic and glass fibers, and yet is transparent or nearly transparent or translucent so as to visually blend with the natural color of the teeth on which the appliances are mounted.

BRIEF SUMMARY OF THE INVENTION

The invention is an orthodontic appliance having a portion under tensile load by which force is applied to the teeth of a patient, wherein the portion is comprised at least in part of mesoporous material. In the preferred embodiment the orthodontic appliance is comprised substantially of mesoporous metal. In particular the orthodontic appliance has an archwire and the archwire is composed at least in part or substantially of mesoporous metal.

The mesoporous material is characterized by being at least in part transparent to visible light or at least translucent to visible light. The mesoporous material is characterized by having manufactured pores therein with a maximum linear dimension of the order of tens of nanometers. Alternatively, the mesoporous material is characterized by having pores therein less than 400 nm in diameter. Thus, the mesoporous material has pores defined therein which constitutes between 25% to 75% by volume of the portion or more. Preferably the mesoporous material is comprised of an alloy of metals chosen for tensile strength.

The invention can be better visualized by turning to the following drawing wherein like elements are referenced by like numerals.

The invention having been illustrated by the foregoing drawings, turn now to the following detailed description wherein the illustrated embodiment is set out by way of example.

DETAILED DESCRIPTION OF THE PREFERRED EMBODIMENTS

Figure 1:
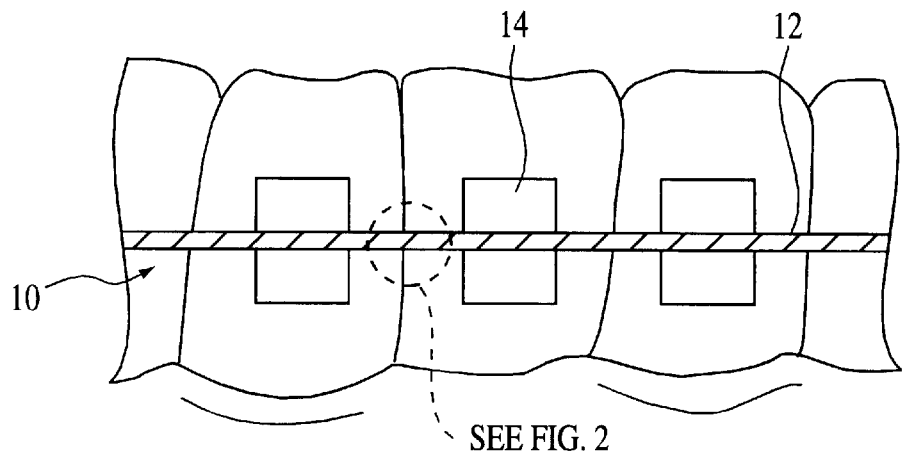
FIG. 1 is a front elevation view of teeth fitted with brackets and an archwire using mesoporous metal.
Figure 2:
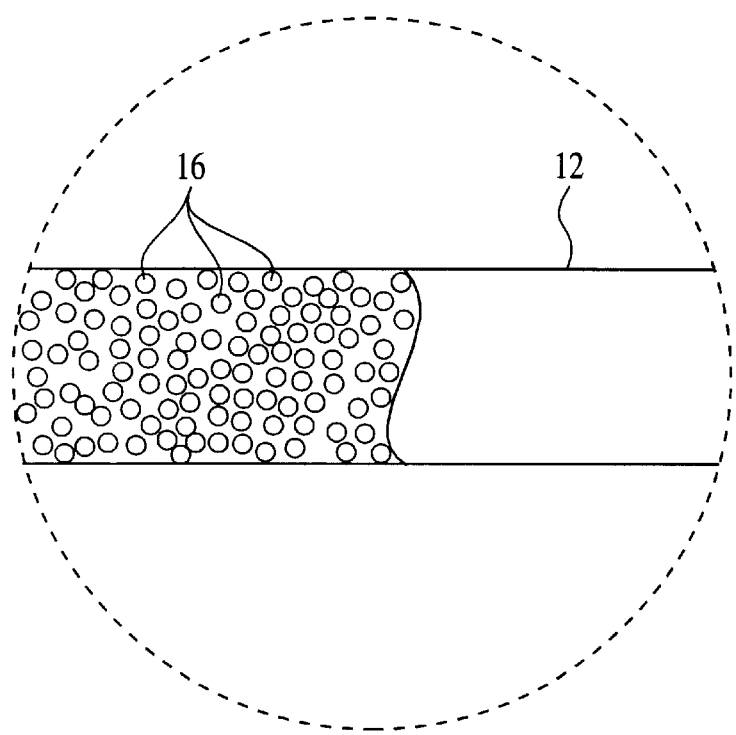
FIG. 2 is an enlargement of the elevational view of FIG. 1 showing the open pores of the archwire.

An orthodontic appliance, generally denoted in the elevational view of FIG. 1 by reference numeral 10, made from mesoporous metals is substantially transparent or at least translucent so that it presents a cosmetic appearance having a color the same as or similar to the natural dental services to which the appliance is applied. The archwires 12 and brackets 14 of the orthodontic appliance 10 are fabricated from mesoporous metal and metal alloys, which have pores 16 defined therein as shown in the enlarged view of FIG. 2 of the diameter less than the shortest wavelength of visible light incident on appliance 10 and with a density of pores 16 such that the average index of a fraction of the mesoporous metal is closer to that of air than to the solid metal from which the dental appliance is fabricated. The small size of the pores 16 means that the dental appliance 10 is a poor scatterer of light while the high density of pores 16 means that the optical properties of the mesoporous metal on the average tend to match those of air as opposed to the solid metal, thus making the mesoporous metal transparent or at the very least translucent. Nevertheless, the mesoporous metal in the form of brackets 14 and archwire 12 is still able to carry high tensile loads as may be required to apply corrective forces to maloccluded teeth within an orthodontic appliance. Archwire 12 is shown as a solid single strand, but it must be understood that braided or multistranded combinations of mesoporous wires can also be used if desired.

Mesoporous metals have become recently available as materials which have metallic tensile strengths while being transparent or translucent. A mesopore solid is material with a orderly structure of tiny pores 16, typically a few tens of nanometers across in diameter. The pores 16 are made using a process that employs tiny sacrificial silica spheres to define the pores structure. The spheres which may be approximately 40 nm in diameter on the average, are packed together in a regular pattern like stacked fruit and then heated to about 800° C. so that they stick together. The even tinier gaps between the spheres are chemically filled with a second material, which in the present invention is a high tensile strength metallic powder, which may include an alloy of materials chosen for high tensile strength. Finally the spheres are dissolved away using hydrochloric acid or another suitable etchant. The method and composition of mesoporous metals is conventional and will thus not be further detailed.

It must be understood that the development of mesoporous metals is rapidly evolving so that the scope of the invention is meant to include those mesoporous metals now known and later devised. Thus while it is contemplated that high tensile strength mesoporous materials will be metallic in nature, it is entirely within the scope of the invention that nonmetallic or semi-metallic systems may be equivalently employed as long as the tensile strength is sufficient to carry the loads required in orthodontic applications.

The result is a solid which is a honeycomb of tightly packed spherical pores 16 so that up to 75% of the volume of the solid is empty space, a metallic foam as it were. Since the spacing in the pores 16 is much less than the wavelength of visible light which ranges from 400–750 nm, the resulting solid scatters light very weakly and thus appear transparent or translucent. Such porous metals are well known to the art and are fabricated for example by Thomas Mallouk at Pennsylvania State University. Vicki Colvin at Rice University has also fabricated pieces of porous metal characterized by transparency. The color of the porous metal varies depending upon the diameter of the pore size, which in turn is varied by using different sized sacrificial spheres.

In the illustrated embodiment, it is anticipated that the archwire 12 and brackets 14 are formed by conventional means such as molding or drawn out by wire dies while the spheres are still embedded in the metallic matrix. After the forming of the object the spheres are dissolved out of the matrix with hydrochloric acid or another etchant. Thereafter the orthodontic appliances are manufactured and assembled and installed in the patient by conventional means.

While a preferred embodiment the material used to make the archwires 12 brackets 14 and other appliances is transparent or nearly transparent, it is also acceptable that the materials may be translucent or have a slight coloring of their own. For example, many mesoporous metals are translucent with a smoky haze, which nevertheless is substantially less visible at a distance when installed on a patient's teeth than conventional metal archwires 12.

It is also anticipated that the thickness or diameter of the archwires 12 and brackets 14 may have to be increased in order to compensate for the slightly lower tensile strength of a highly porous metal wire or bracket 14 than with a solid metal wire or bracket 14. Nevertheless, within reason the size of the archwires 12 and brackets 14 does not dramatically affect the visual appearance of the appliances as much as its opacity or rather its lack of transparency.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An orthodontic appliance having a portion under tensile load by which force is applied to the teeth of a patient, wherein the portion is comprised at least in part of mesoporous material.

2. The orthodontic appliance of claim 1 wherein the portion is comprised substantially of mesoporous metal.

3. The orthodontic appliance of claim 1 having an archwire, wherein the archwire is composed at least in part of mesoporous metal.

4. The orthodontic appliance of claim 1 having an archwire, wherein the archwire is composed substantially of mesoporous metal.

5. The orthodontic appliance of claim 1 wherein the mesoporous material is characterized by being at least in part transparent to visible light.

6. The orthodontic appliance of claim 1 wherein the mesoporous material is characterized by being translucent to visible light.

7. The orthodontic appliance of claim 1 wherein the mesoporous material is characterized by having manufactured pores therein with a maximum linear dimension of the order of tens of nanometers.

8. The orthodontic appliance of claim 1 wherein the mesoporous material is characterized by having pores therein less than 400 nm in diameter.

9. The orthodontic appliance of claim 1 wherein the mesoporous material has pores defined therein which constitutes at least 75% by volume of the portion.

10. The orthodontic appliance of claim 1 wherein the mesoporous material has pores defined therein which constitute at least 50% volume of the portion.

11. The orthodontic appliance of claim 1 wherein the mesoporous material has pores defined therein which constitute at least 25% by volume of the portion.

12. The apparatus of claim 1 wherein the mesoporous material is comprised of an alloy of metals chosen for tensile strength.

13. An improvement in an orthodontic device having archwires which are comprised at least in part of a mesoporous material.

14. The improvement of claim 13 wherein the archwires are comprised substantially of mesoporous material.

15. The improvement of claim 13 wherein the mesoporous material is a mesoporous metal.

16. The improvement of claim 15 wherein the mesoporous metal is a mesoporous metal alloy.

17. The improvement of claim 13 wherein the mesoporous material is characterized by pores of 400 nm in maximum linear dimension or less.

18. The improvement of claim 13 wherein the archwires are transparent.

19. The improvement of claim 13 wherein the archwires are translucent.

20. The improvement of claim 13 further comprising brackets composed of mesoporous material.

* * * * *